(12) United States Patent
Seifert et al.

(10) Patent No.: US 6,667,401 B2
(45) Date of Patent: Dec. 23, 2003

(54) METHOD FOR PRODUCING HETEROCYCLIC COMPOUNDS

(75) Inventors: Hermann Seifert, Bergisch Gladbach (DE); Uwe Stelzer, Burscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/048,710
(22) PCT Filed: Jan. 8, 2001
(86) PCT No.: PCT/EP01/00125
§ 371 (c)(1), (2), (4) Date: Mar. 26, 2002
(87) PCT Pub. No.: WO01/53296
PCT Pub. Date: Jul. 26, 2001

(65) Prior Publication Data
US 2003/0114667 A1 Jun. 19, 2003

(30) Foreign Application Priority Data
Jan. 19, 2000 (DE) .......................... 100 02 049

(51) Int. Cl.$^7$ ................... C07D 417/00; C07D 401/00; C07D 211/72; C07D 211/84; C07D 213/26
(52) U.S. Cl. .................. 546/269.7; 546/270.7; 546/274.7; 546/345; 546/346; 546/271.4; 546/276.4; 546/193; 544/55; 544/96; 544/331
(58) Field of Search .......................... 546/269.7, 274.7, 546/345, 346, 193, 270.7, 271.4, 276.4; 544/55, 96, 331

(56) References Cited

U.S. PATENT DOCUMENTS

| | | | |
|---|---|---|---|
| 4,803,277 A | 2/1989 | Shiokawa et al. | 514/332 |
| 4,882,344 A | 11/1989 | Shiokawa et al. | 514/342 |
| 4,988,712 A | 1/1991 | Shiokawa et al. | 514/340 |
| 5,118,689 A | 6/1992 | Oinuma et al. | 514/300 |
| 5,179,095 A | 1/1993 | Oinuma et al. | 514/249 |
| 5,198,549 A | 3/1993 | Günther | 546/345 |
| 6,307,053 B1 | 10/2001 | Yeh et al. | 546/274.7 |

FOREIGN PATENT DOCUMENTS

| | | |
|---|---|---|
| DE | 38 30 238 | 3/1990 |
| EP | 0 163 855 | 12/1985 |
| EP | 0 235 725 | 9/1987 |
| EP | 0 260 485 | 3/1988 |
| EP | 1 024 140 | 8/2000 |

OTHER PUBLICATIONS

JACS, 79, Jul.–Sep. 1957, pp. 3565–3566, Ellis V. Brown, Preparation and Reactions Of 2–Nitropyridine–1–oxides.
Arch. Pharm. 305, (month unavailable) 1972, pp. 731–737, R. Neidlein und H. Reuter, Reaktionsverhalten von N–Cyanimido–dithiokohlensäureester und 2,2–Bismethylmercaptio–1–cyanacrylnitril.
Biosci Biotech. Biochem., 56, (month unavailable) 1992, Koichi Moriya, Katsuhiko Shibuya, Yumi Hattori, Shin–ichi Tsuboi, Kozo Shiokawa and Shinzo Kagabu, 1–(6–Chloronicotinyl)–2–nitroimino–imidazolidines and Related Compounds as Potential New Isecticides.
Biosci. Biotechnol. Biochem, 57 (month unavailable) pages 127–128, Koichi Moriya, Katsuhiko Shibuya, Yumi Hattori, Shini–ichi Tsuboi, Kozo Shiokawa and Shinzo Kagabu, Structural Modification of the 6–Chloropyridyl Moiety in the Imidacloprod Skeleton: Introduction of a Five–membered Heteroaromatic Ring and the Resulting Insecticidal Activity.
Heterocycles, 31 (month unavailable) 1990, pp. 1601–1604, Chuzo Iwata, Michitaro Fujimoto, Shigeha Okamoto, Chihiro Nishihara, Masatoshi Sakae, Masanori Katsurada, Mayumi Watanabe, Tetsuya Kawakam, Tetsuaki Tanaka and Takeshi Imanish, The Reaction of 3–Substituted 2–(N–Cyanoimino)Thiazolidine Derivatiaves with Hydrazine: Novel Synthesis of Triazoles.

*Primary Examiner*—John M. Ford
*Assistant Examiner*—Zachary C. Tucker
(74) *Attorney, Agent, or Firm*—Richard E. L. Henderson; John E. Mrozinski, Jr.

(57) ABSTRACT

The present invention relates to a process for the preparation of compounds of the formula (I)

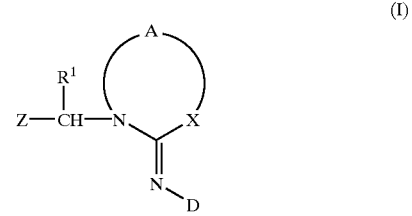

in which $R^1$, A, D, X and Z have the meanings given in the description,
by reacting compounds of the formula (II)

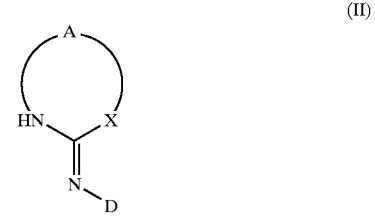

in which
A, D and X have the meanings given above,
with a base and in the presence of a diluent, and subsequently reacting the reaction mixture with the mixture of CCMP/CMP (2-chloro-5-chloromethylpyridine/2-chloro-5-methylpyridine) and the corresponding hydrochlorides.

8 Claims, No Drawings

METHOD FOR PRODUCING HETEROCYCLIC COMPOUNDS

This application was filed under 35 U.S.C. 371 as the U.S. national stage of PCT/EP01/00125, filed Jan. 8, 2001.

FIELD OF THE INVENTION

The present invention relates to a novel process for the preparation of known heterocyclic compounds.

BACKGROUND OF THE INVENTION

The preparation of unsaturated, heterocyclic compounds by the alkylation of unsubstituted ring substance atoms, which can be carried out, inter alia, in alcohol (EP-A-259 738), is known.

Also known are alkylation reactions in aprotic solvents (EP-A-259 738).

In these cases, subsequent purification of the product is necessary in order to achieve adequate purity, and in addition the yields which can be achieved with the known processes are unsatisfactory.

DETAILED DESCRIPTION OF THE INVENTION

We have found that compounds of the formula (I)

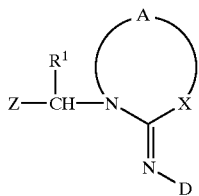

(I)

in which
- $R^1$ is a hydrogen atom or an alkyl group,
- A is an ethylene group which may be substituted by alkyl, or a trimethylene group which may be substituted by alkyl,
- D is nitro or cyano,
- X is an oxygen or sulphur atom or the groups

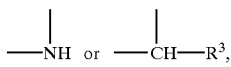

in which
- $R^3$ is a hydrogen atom or an alkyl group, and
- Z is an optionally substituted 5- or 6-membered heterocyclic group which contains at least two heteroatoms chosen from oxygen, sulphur and nitrogen atoms, or is an optionally substituted 3- or 4-pyridyl group, are obtained by reacting compounds of the formula (II)

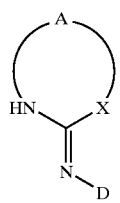

(II)

in which
A, D and X have the meanings given above, with a base and in the presence of a diluent, and then reacting the reaction mixture with the mixture of CCMP/CMP (2-chloro-5-chloromethylpyridine/2-chloro-5-methylpyridine) with the corresponding hydrochlorides.

Surprisingly, the abovementioned compounds can be prepared in a more simple and fewer process steps and in a better yield by the process according to the invention.

In the general formulae (I) and (II), the variables are as follows:
- $R^1$ is preferably hydrogen or a $C_1$–$C_3$-alkyl group, particularly preferably hydrogen;
- A is preferably an ethylene or trimethylene group, each of which may be substituted by a $C_1$–$C_3$-alkyl group, particularly preferably an ethylene group;
- D is nitro or cyano,
- X is preferably an oxygen or sulphur atom or the group

particularly preferably an oxygen atom or the group

Z is preferably a halogenated, 5- or 6-membered heterocyclic group which contains 2 heteroatoms chosen from the group oxygen, sulphur and nitrogen, or is a halogenated 3- or 4-pyridyl group, particularly preferably a halogenated thiazolyl or 3-pyridyl group, very particularly preferably 2-chloropyrid-5-yl.

A very particularly preferred compound of the formula (I) is the compound of the formula (Ia)

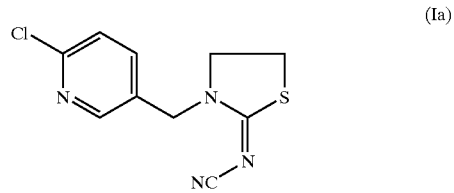

(Ia)

which is obtained by reacting the compound of the formulae (IIa)

(IIa)

with a base and in the presence of a diluent, and by subsequently reacting the reaction mixture with a mixture of CCMP/CMP with the corresponding hydrochlorides.

A further very particularly preferred compound of the formula (I) is the compound of the formula (Ib)

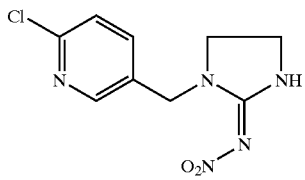

(Ib)

which is obtained by reacting the compound of the formula (IIb)

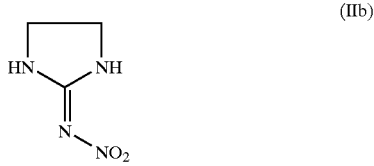

(IIb)

with a base and in the presence of a diluent, and by subsequently reacting the reaction mixture with a mixture of CCMP/CMP with the corresponding hydrochlorides.

Solvents which can be used are protic and dipolar-aprotic solvents, in particular water, alcohols, ketones (preferably MIBK), esters (preferably butyl acetate), nitriles (preferably acetonitrile, n-propionitrile, butyronitrile), pyridines (preferably CMP), amides (DMF), DMSO or carbonates, or mixtures thereof with water. If alcohols are used as solvents, the compounds of the formula (I) can be obtained directly in a modification advantageous for use as crop protection agents and in the necessary purity.

Examples of alcohols which may be used are:

primary alcohols, such as methanol, ethanol, propanol, butanol, 2-methyl-1-propanol, 1-pentanol, benzyl alcohol, secondary alcohols, such as isopropanol, sec-butanol, 2-pentanol, tert-alcohols, such as tert-butanol.

Particularly preferred solvents are alcohols which are immiscible or only partially miscible with water (such as n-butanol, amyl alcohol, in particular n-butanol) or nitriles which are immiscible or only partially miscible with water (such as n-propionitrile or butyronitrile, in particular n-propionitrile).

The process may be carried out in the presence of a base. Examples which may be mentioned are: alkali metal and alkaline earth metal hydroxides, such as NaOH, KOH, $Ca(OH)_2$, alkali metal carbonates or hydrogencarbonates, such as $Na_2CO_3$, $Li_2CO_3$, $K_2CO_3$, $Cs_2CO_3$ or $NaHCO_3$ and $KHCO_3$. Preference is given to $K_2CO_3$, NaOH and $KHCO_3$, in particular $K_2CO_3$.

The compounds of the general formula (II) can also be used as alkali metal salt or alkaline earth metal salt in solid or dissolved form.

When working in water, water-alcohol or water-nitrile mixtures, the process is carried out at a pH range between 6 and 13.

Catalysts which can be used are phase transfer catalysts, where appropriate quaternary ammonium halides, such as tetrabutylammonium bromide or chloride, or Cs salts etc.

The reaction can also be carried out by initially introducing the compounds of the general formula (II), optionally as alkali metal or alkaline earth metal salt, and heating them in the presence of a base at temperatures of from 40° C. to 130° C., optionally under reduced pressure, preferably at 100 to 500 mbar, and then adding the CCMP/CMP mixture at 50 to 90° C., optionally under reduced pressure, preferably at 60° C. to 80° C.

The reaction is expediently carried out under atmospheric pressure, although it is also possible to work under reduced or elevated pressure. Particular preference is given to carrying out the reaction under reduced pressure.

The process is carried out in practice by reacting, for example, 1 mol of a mixture of CCMP/CMP with 0.95 to 3 mol of the compounds of the formula (II), preferably 1.0 to about 2.5 mol, in a solvent such as butanol in the presence of from 1 to 3 mol, preferably 1.5 to 2.5 mol, of a base such as, for example, potassium carbonate and optionally in the presence of a catalyst such as tetrabutylammonium bromide or cesium carbonate.

If water is used in a two-phase system, preference is given to working at pH8–10.

The reaction time is between 3 and 12 hours, preferably 5 to 10 hours. When the reaction is complete, the solvent may be changed if necessary. Here, the majority of the reaction diluent is distilled off under reduced pressure (1–1000 mbar) and the quantity is topped up by one of the abovementioned diluents. Solvent substitution can take place before or after the hydrolysis.

The suspension from the reaction is hydrolysed at a temperature of from 50° C. to 100° C., and the organic phase is separated off at 50° C. to 80° C. This phase is cooled, and the precipitated active ingredient is isolated, washed and recrystallized.

The CMP present in the mother liquor (temperature range 50° C. to 130° C., pressure range 1–1000 mbar) can be recovered and returned to the process: the mother liquor obtained can be admixed with the diluent from the crystallization (1 part of mother liquor/4 parts of solvent—1 part of mother liquor/0.5 parts of solvent), the suspension is cooled and the precipitated active ingredient is filtered off.

The starting materials of the formula (II) are known and/or can be prepared by processes known per se (cf. JACS 79, (1957), 3565; Arch. Pharm. 305, (1972), 731–736; Heterocycles 31 (1990), 1601–1604; Biosci. Biotechnol. Biochem. 57, (1993), 127–128; Biosci. Biotechnol. Biochem. 56, (1992), 364–365).

The preparation of 2-chloro-5-chloromethylpyridine is carried out analogously to the described process (EP-A-458 109, EP-A-260 485). The 2-chloro-5-methylpyridine is chlorinated in an organic solvent (acetonitrile, carbon tetrachloride, water pH-controlled) using a free-radical initiator (AIBN) at the boil. The conversion of the reaction is terminated at about 40% in order to obtain a high selectivity of 2-chloro-5-chloromethylpyridine. Distillation of the organic solvent under reduced pressure is then carried out.

Following distillation of the solvent, the mixture of CCMP/CMP comprises 5–15% residual solvent, 30–50% CMP and 25–45% CCMP with the corresponding hydrochlorides.

This mixture of 2-chloro-5-methylpyridine and 2-chloro-5-chloromethylpyridine and the corresponding hydrochlorides serves as seed substance for the active ingredient reaction. This mixture can be used in this reaction in undiluted form or in a diluent which is expediently also used in the active ingredient reaction.

The compounds of the formula (I) are, for example, suitable for use as insecticides (EP A2 0235 752, EP A2 0259 738).

The examples below illustrate the subject matter of the invention without limiting it in any way.

EXAMPLE 1

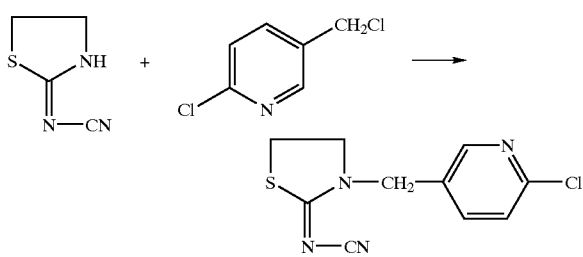

0.615 mol of potassium carbonate and 0.3 mol of 2-cyanoiminothiazolidine are suspended in 100 ml of n-butanol and stirred at 60° C. for 1 h. Over the course of 2 h, 0.315 mol of 2-chloro-5-chloromethylpyridine/2-chloro-5-methylpyridine (CCMP/CMP, 23% CCMP in the mixture), suspended in 100 ml of n-butanol, are added at 70° C., and the mixture is stirred at 72° C. for 2 h. After cooling to 65° C., 400 g of water are added and the phases are separated. The organic phase is then stirred at 50° C. for 3 h and then at −5° C. for 18 h. Precipitated product is filtered off and dried; 59.6 g (78% of theory).

EXAMPLE 2

0.615 mol of potassium carbonate and 0.3 mol of 2-cyanoiminothiazolidine are suspended in 100 ml of n-butanol and stirred at 60° C. for 1 h. Over the course of 2 h, 0.315 mol of 2-chloro-5-chloromethylpyridine/2-chloro-5-methylpyridine (CCMP/CMP, 23% CCMP in the mixture), suspended in 100 ml of n-butanol, are added at 70° C., and the mixture is stirred at 72° C. for 2 h. After cooling to 65° C., 400 g of water are added and the phases are separated. The organic phase is then stirred at 50° C. for 3 h and then at −5° C. for 18 h. Precipitated product is filtered off and dried. The mother liquor is admixed with butanol in the ratio 1:1 and cooled to 0° C., and the solid which precipitates out during cooling is filtered off and dried. Total yield: 66.1 g (85% isolated product).

EXAMPLE 3

0.3 mol of 2-cyanoiminothiazolidine and 4.2 g of tetrabutylammonium bromide are suspended in 300 ml of water and heated to 70° C. 0.315 mol of CMP/CCMP mixture are added. NaOH is used to continuously keep the pH of the reaction mixture at 8 to 8.5. After a reaction time of 2 h at 60° C., phase separation is carried out at this temperature and the organic phase is diluted with 150 ml of butanol and stirred. Over the course of 3 h, the mixture is cooled to 3° C. and precipitated product is filtered off with suction; 58.5 g (76% of theory) are obtained in this way.

EXAMPLE 4

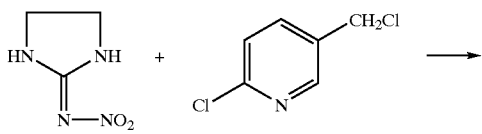

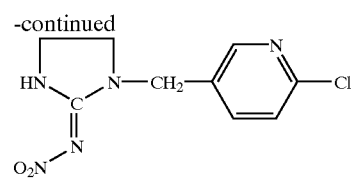

1.5 mol of ethylene nitroguanidine (comprises 16.5% $H_2O$) are taken up in 600 g of n-propionitrile, and the water is removed by azeotropic distillation. 342 g of potassium carbonate (2.5 mol) are then added at 95° C. 2 g of cesium carbonate are then added. Over the course of 30 minutes, 521 g of CMP/CCMP (31% CCMP) are added at 95–100° C. After a reaction time of 5 h at 100–105° C., 1.2 l of water are added. HCl is used to maintain the pH of the reaction mixture at 6 to 7. The propionitrile is distilled off from the organic phase at 180 mbar. 500 g of n-butanol are then added, and the mixture is heated to 80° C. and the phases are separated. The organic phase is cooled to 0° C. Precipitated product is filtered off and dried; 187.4 g (73% of theory).

What is claimed is:

1. A process for the preparation of compounds of the formula (I)

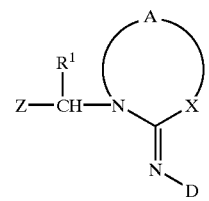

wherein $R^1$ represents a hydrogen atom,

A represents an ethylene group which may be substituted by alkyl, or a trimethylene group which may be substituted by alkyl, D represents nitro or cyano, X represents an oxygen or sulphur atom or the groups

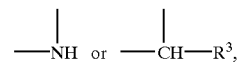

wherein $R^3$ represents a hydrogen atom or an alkyl group, and

Z represents 2-chloropyrid-5-yl, said process comprising
(a) reacting with a base, in the presence of a diluent, a compound of the formula (II)

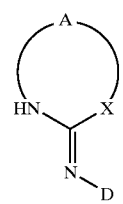

wherein A, D and X are as defined above, to yield a reaction mixture (b) reacting said reaction mixture with a mixture of CCMP/CMP (2-chloro-5-chloromethylpyridine/2- chloro-5-methylpyridine) with the corresponding hydrochlorides; and (c) collecting the reaction product.

2. The process of claim 1, wherein, $R^1$ represents hydrogen or a $C_1$–$C_3$-alkyl group;

A represents an ethylene or trimethylene group, which may be substituted by a $C_1$–$C_3$-alkyl group;

D represents nitro or cyano,

X represents an oxygen or sulphur atom or the group

and

Z represents 2-chloropyrid-5-yl.

3. The process of claim 1, wherein, $R^1$ represents hydrogen;

A represents an ethylene group;

D represents nitro;

X represents the group

and

Z represents 2-chloropyrid-5-yl.

4. A process according to claim 1 wherein the diluent is an alcohol or nitrile that is immiscible or only partially miscible with water.

5. A process according to claim 4 wherein the diluent is n-butanol, amyl alcohol, n-propionitrile, or butyronitrile.

6. A process according to claim 1 wherein the mixture of CCMP/CMP (2-chloro-5-chloromethyl pyridine/2-chloro-5-methylpyridine) with the corresponding hydrochlorides is obtained by chlorinating CMP in an organic solvent using a free-radical initiator at the boil, terminating the chlorination at about 40% completion, and distilling off the organic solvent under reduced pressure.

7. A process according to claim 6 wherein the mixture of CCMP/CMP (2-chloro-5-chloromethyl pyridine/2-chloro-5-methylpyridine) with the corresponding hydrochlorides following distillation of about 5 to about 15% residual solvent, about 30 to about 50% CMP, and about 25 to about 45% CCMP with the corresponding hydrochlorides.

8. A process according to claim 1 wherein the compound of the formula (ii) is a compound of formula (IIa) or formula (IIb)

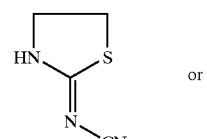 (IIa)

or

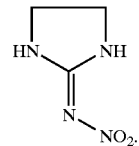 (IIb)

* * * * *